(12) United States Patent
Azar et al.

(10) Patent No.: US 7,470,270 B2
(45) Date of Patent: Dec. 30, 2008

(54) ACNE TREATMENT

(75) Inventors: Zion Azar, Shoham (IL); Pinchas Shalev, Kfar-Saba (IL)

(73) Assignee: Radiancy Inc., Orangeburg, NY (US)

( * ) Notice: Subject to any disclaimer, the term of this patent is extended or adjusted under 35 U.S.C. 154(b) by 597 days.

(21) Appl. No.: 10/481,987

(22) PCT Filed: Jun. 27, 2001

(86) PCT No.: PCT/IL01/00587

§ 371 (c)(1),
(2), (4) Date: Dec. 24, 2003

(87) PCT Pub. No.: WO03/002009

PCT Pub. Date: Jan. 9, 2003

(65) Prior Publication Data

US 2004/0167498 A1   Aug. 26, 2004

(51) Int. Cl.
*A61B 18/18* (2006.01)
(52) U.S. Cl. .................. 606/9; 607/88; 607/89; 128/898
(58) Field of Classification Search .............. 606/9; 607/88–92; 128/898
See application file for complete search history.

(56) References Cited

U.S. PATENT DOCUMENTS

| | | |
|---|---|---|
| 5,059,192 A | 10/1991 | Zaias |
| 5,226,907 A | 7/1993 | Tankovich |
| 5,405,368 A | 4/1995 | Eckhouse |
| 5,425,728 A | 6/1995 | Tankovich |
| 5,540,660 A | 7/1996 | Jenson |
| 5,549,660 A | 8/1996 | Mendes et al. |
| 5,620,478 A | 4/1997 | Eckhouse |
| 6,036,684 A | 3/2000 | Tankovich et al. |
| 6,168,590 B1 * | 1/2001 | Neev ............... 606/9 |
| 6,187,001 B1 | 2/2001 | Azar et al. |
| 6,214,034 B1 | 4/2001 | Azar |
| 6,228,074 B1 * | 5/2001 | Almeida ............ 606/9 |
| 6,235,016 B1 * | 5/2001 | Stewart ............ 606/9 |
| 6,283,956 B1 | 9/2001 | McDaniel |
| 6,408,212 B1 * | 6/2002 | Neev ............. 607/100 |
| 6,600,951 B1 * | 7/2003 | Anderson ......... 604/20 |

FOREIGN PATENT DOCUMENTS

| | | |
|---|---|---|
| CN | 1086418 | 5/1994 |
| EP | 0 736 308 | 10/1996 |
| EP | 0 788 814 | 8/1997 |

(Continued)

OTHER PUBLICATIONS

Jenifer R. Lloyd, Mirko Mirkov "Selective photothermolysis of the sebaceous glands for acne treatment," Lasers in Surgery and Medicine, vol. 31, Issue 2 , pp. 115-120; Published Online: Aug. 6, 2002; Copyright © 2002 Wiley-Liss, Inc. See http://www3.interscience.wiley.com/cgi-bin/abstract/97517649/ABSTRACT?CRETRY=1&SRETRY=0).*

(Continued)

*Primary Examiner*—Ahmed M Farah

(57) ABSTRACT

A method and apparatus (100) are provided for treating acne using pulsed radiant energy (246) to destroy or partially destroy one or more hairs (112), without damaging the skin, or, alternatively, to destroy or partially destroy one or more acne-related structures without damaging either skin or hair.

24 Claims, 2 Drawing Sheets

FOREIGN PATENT DOCUMENTS

| | | |
|---|---|---|
| JP | 07-100182 | 4/1995 |
| WO | WO 99/34867 | 7/1999 |
| WO | WO 99/43387 | 9/1999 |
| WO | WO 99/49937 | 10/1999 |
| WO | WO 99/58195 | 11/1999 |

OTHER PUBLICATIONS

Shalita, A. R. et al.; "Acne PhotoClearing (APC™) Using a Novel, High-Intensity, Enhanced, Narrow-Band, Blue Light Source;" Clinical Application Notes; vol. 9, No. 1.

"Disorders of Hair Follicles and Sebaceous Glands;" The Merck Manual of Diagnosis and Therapy; Chapter 116; Section 10—Dermatologic Disorders; pp. 811-816.

"Apendages of Skin;" Dental System; Integumental System; pp. 400-407.

Anderson et al.; "Selective Photothermolysis: Precise Microsurgery by Selective Absorption of Pulsed Radiation;" Apr. 29, 1983; Science; vol. 220; pp. 524-527.

* cited by examiner

ACNE TREATMENT

RELATED APPLICATIONS

The present application is a U.S. national application of PCT Application No. PCT/IL01/00587, filed Jun. 27, 2001.

1. Field of the Invention

The present invention relates to treating acne with heat and more specifically to a method of applying heat to preferentially destroy or partially destroy hair follicles, sebaceous glands and/or other acne-associated structures so that acne is ameliorated or eradicated without damaging the skin.

2. Background of the Invention

Acne is an inflammatory disease of pilosebaceous glands in which, it is believed, blockage of the hair follicle leads to formation of comdones (i.e., blackheads or whiteheads), composed of sebum, keratin and microorganisms, notably *Propionibacterium acnes* (*P. acnes*). It is further believed that *P. acnes* breaks down the sebum and keratin into products that irritate the hair follicle, resulting in inflammation, abscess or cyst formation or scaring in severe cases. Acne affects teenagers and adults, sometimes up to the age of 55.

Topical treatments include Benzoyl peroxide to kill bacteria and dry the skin, salicylic acid to help unclog follicles, and sulfur to unclog follicles and help break down blackheads and whiteheads. Vitamin A derivatives, called retinoids, are used topically to speed up the shedding of skin, to help unclog follicles. Systemic antibiotics and/or oral retinoids, such as Accutane, are usually more effective but are reserved for severe cases of acne because they have more serious side effects.

Heat lamps are also utilized to alleviate acne symptoms, presumably promoting unplugging of the follicles and drainage of the infection. Similarly, extended exposure to the sun and the use of ultraviolet lamps are known to help ameliorate acne symptoms.

According to a prior art depilatory treatment, (Tankovich, U.S. Pat. Nos. 5,425,728 and 5,226,907, the disclosures of which are incorporated herein by reference) a contaminant, such as graphite, having a high absorption of a wavelength of light is applied to a section of skin. The skin is illuminated with short laser pulses at the matching wavelength to destroy hair structures. It is believed that this depilatory method could not be utilized in treating acne because the contaminant irritates the skin and, in the presence of acne, exacerbates the acne symptoms.

In another prior art depilatory treatment, (Eckhouse, EPO 736308 and EPO 788814, the disclosures of which are incorporated herein by reference) a filtered light between 600 and 1300 nanometers is applied to the skin over which a gel has been applied. The hair absorbs the light and heats to approximately 70° C., causing destruction of the hair follicle, thus destroying the hair. The gel applied to the skin acts as a heat sink to keep the skin from reaching the temperature at which heat damage occurs. This system does not teach the treatment of acne.

A prior art system (U.S. Pat. No. 5,540,660, the disclosure of which is incorporated herein by reference) for treating acne utilizes a plurality of LEDS to illuminate the patient's skin in a small area including acne. There is no provision in the described system for preventing skin damage during treatment. However, little or no heat is generated by the radiation level of LEDs.

A. R. Shalita MD, et al, in *Clinical Application Notes* Vol. 9 No. 1, "Acne Photo Clearing Using a Novel, High Intensity Enhanced, Narrow Band Blue Light Source," the disclosure of which is incorporated herein by reference, reports using a specific band of light for acne treatment that is absorbed by photoporphyrin. The resultant excitation of photoporphyrin, a chemical produced by *P. acnes*, destroys some of the *P. acnes* bacteria. This method does not specifically target the acne-producing structures and demonstrates an improvement in only 60% of the cases after eight weeks of treatment.

Selective photothermolysis was introduced by Anderson and Parrish in 1983 ("Selective Photothermolysis: Precise Microsurgery by Selective Absorption of Pulsed Radiation," *Science*, Vol. 220, pp. 524-527), the disclosure of which is incorporated herein by reference, in which the tissue to be destroyed is characterized by significantly greater optical absorption at some wavelength of electromagnetic radiation than the surrounding tissue. The pulse length is kept on the order of the target's thermo-relaxation time, preventing heat damage to the surrounding skin.

Another prior art system (described in WO 99/449937, the disclosure of which is incorporated herein by reference) directly heats, by selectively absorbed radiation, lipid-rich tissue, such as sebaceous glands, thereby causing destruction of related structures such as hair follicles and acne. To prevent skin damage, a cryogenic material is applied to the skin. As the cryogenic material is non-selective, it likely cools the pilosebaceous plug, preventing drainage of the acne infection. The heat absorbed by the lipid rich tissue may be conducted to a hair follicle, killing the hair.

A prior art system for depilation, based upon photothermolysis is shown in U.S. Pat. No. 6,187,001, the disclosure of which is incorporated by reference. In this method, radiant energy raises the temperature of the skin and hair. Then, heat is conducted into the follicle via the hair from the air outside the skin, destroying the follicle. The initial heating of the skin and hair raises their temperature so that the duration and intensity heating required to kill the hair, via conduction into the follicle, is reduced, preventing damage by heating in the surrounding tissue. Treatable tissue includes birtbmarks, port wine stains, spider veins, and varicose veins. This patent does not indicate use as a treatment for acne.

SUMMARY OF THE INVENTION

According to an aspect of some embodiments of the present invention, in a treatment for acne, heat is conducted through a hair into the hair follicle, destroying the hair follicle and providing diminishment or resolution of acne.

Alternatively or additionally, heat is conducted through a hair into the hair follicle and/or one or more acne-related structures, destroying the hair follicle and/or one or more acne-related structures, providing diminishment or resolution of acne. Acne-related structures include, but are not limited to a sebaceous gland, a papilla, bacteria such as *Propionibacterium acnes* bacteria, an acne cyst or nodule, an acne papule, an acne pistule, intrafollicular hyperkeratosis, a pilosebaceous follicle blockage comprising a closed comedone (whitehead) or an open comedone (blackhead), a pseudofolliculitis (ingrown hair), a sweat gland, a sweat gland duct and a hemorrhagic follicular plug.

Heating hair is generally accomplished by radiation or by heat conducted into the hair from outside the skin. In accordance with some embodiments of the invention, the heat reaches the hair at least partly by conduction from the air outside the skin as, for example, in the above referenced U.S. Pat. No. 6,187,001.

In an exemplary embodiment, the temperature of the hair and skin is raised, for example using pulsed radiant energy, prior to conduction of heat into the follicle by the hair and destruction of the hair and one or more acne-related structures. Such radiant energy can be, for example, from a white light of a high-intensity lamp, optionally through a suitable wavelength selection device such as a filter, a broadband electromagnetic radiation, or a laser beam in a suitable wavelength that is readily absorbed by acne-related structures.

In an exemplary embodiment, raising the ambient temperature of the skin and hair lowers the intensity and/or duration of heat required to destroy the hair follicle and acne-related structures through heat conduction, so the skin temperature is not raised to the point where damage takes place. Alternatively, the skin and hair heating process lowers the temperature gradient between the skin and hair, so that the heat absorbed through the hair and conducted to the hair follicle and acne-related structures is less rapidly conducted into the skin, preventing damage to the skin.

According to an aspect of some embodiments of the present invention, after at least partially destroying a hair by any means, resolution or amelioration of acne symptoms is provided by heating the air surrounding the skin by any means. Such heat can be, for example, using the methods described in the above referenced U.S. Pat. No. 6,187,001. Additionally or alternatively, pulsed radiant energy is from a white light of a high-intensity lamp through a suitable wavelength selection device such as a filter.

Alternatively or additionally, the pulsed radiant energy is broadband electromagnetic radiation.

Alternatively or additionally, the pulsed radiant energy is monochromatic electromagnetic radiation such as from a laser beam. Such pulsed radiant energy can be, for instance, from a laser beam of a wavelength suitable to be preferentially absorbed by one or more of a plurality of hair and or acne-related structures.

The heat is conducted to an acne-related structure, causing an increase in drainage of acne-related materials and/or destruction or partial destruction of an acne-related structure.

Drainage occurs, for instance, when follicular blockage is broken-up by the heat, or when heat causes the sebum to expand, forcing the blockage out of the follicle opening.

Additionally or alternatively, after at least partially destroying a hair by any means, heat is conducted into the follicle and/or directly through the skin, causing destruction or partial destruction of one or more acne-related structures noted above.

In an exemplary embodiment, after at least partially destroying a hair by any means, the temperature of the follicle and/or skin is raised prior to destruction of one or more acne-related structures. This lowers the intensity and/or duration of heat required to drain the follicle and/or destroy one or more acne-related structures through heat conduction, so the skin temperature is kept below the temperature where heat damage takes place. Alternatively, raising the ambient temperature of the skin and/or follicle lowers the temperature gradient between the skin, follicle and acne-related structures. The heat absorbed through the hair and conducted to the hair follicle and acne-related structure is less rapidly conducted into the skin, preventing damage to the skin.

According to an aspect of some embodiments of the present invention, in a treatment for acne, heat is applied to the skin on one or more occasions to destroy or partially destroy one or more acne-related structures, without causing damage to the skin or hair.

In an exemplary embodiment, the heat is supplied to the skin by conduction from hot air surrounding the skin. The temperature is maintained below a temperature required to cause hair or skin damage, but above a temperature required to cause destruction or partial destruction of one or more acne-related structures. Additionally or alternatively, the application of the heat is of a brief duration so there is no damage to the skin or hair but destruction or partial destruction of one or more acne-related structures. Additionally or alternatively, the heat is applied briefly to the skin on more than one occasion and builds up in an acne-related structure while it dissipates from the hair and skin, causing at least partial destruction of the acne-related structure without causing damage to the skin or hair.

In an exemplary embodiment of the invention, the heat is pulsed heat having a duration of between 10 and 1000 milliseconds.

There is thus provided, in accordance with an embodiment of the invention, apparatus for treating acne from a region of skin, the apparatus comprising:

a housing having an opening therein, the housing forming a cavity enclosing a volume of air when the opening is placed in contact with the region of skin;

a switchable heat source disposed within the housing that rapidly heats the volume of air to a temperature sufficient to destroy or partially destroy an acne-related structure by conduction of heat from the skin and/or hair, a power source that controllably energizes the heat source.

There is thus provided a method of treating acne comprising:

heating a hair associated with a focus of acne; and conducting energy from the hair to at least one acne-related structure to at least partially destroy the structure.

Optionally, an acne-related structure comprises a structure associated with the acne focus.

Alternatively, said heating is optionally not sufficient to cause damage to the skin.

Optionally, a portion of said heating is generated by coherent radiant energy.

Alternatively, a portion of said heating is optionally generated by incoherent radiant energy.

Optionally, heating a hair comprises:

heating the air outside the skin; and conducting heat by the hair to the acne-related structure.

In some embodiments of the present invention, said heating of the hair causes destruction of the hair.

Optionally, said destruction of the hair comprises at least partial destruction of a hair follicle in which the hair is situated.

In some embodiments of the present invention, said heating is not sufficient to cause damage to a hair.

There is thus provided a method of treating acne comprising:

destroying a hair associated with a focus of acne using heat on a first occasion; and pulsed heating the focus of acne on a second occasion to at least partially destroy an acne-related structure.

Optionally, a portion of said heating is generated by coherent radiant energy incident on the skin.

Alternatively, a portion of said heating is optionally generated by incoherent radiant energy incident on the skin.

In some embodiments of the present invention, at least a portion of said heating is generated by conduction of heat from air outside the skin.

Optionally, at least a portion of said heating is generated by radiant energy that preferentially heats the focus or sebum associated with the focus as compared to the skin.

There is thus provided an apparatus for ameliorating acne symptoms from a region of skin, the apparatus comprising:

a housing having an opening therein, the housing forming a cavity enclosing a volume of air when the opening is placed in contact with the region of skin; and a pulsed heat source disposed within the housing that rapidly heats the volume of air to a temperature sufficient to destroy an acne-related structure by heat conducted via the skin or hair without causing damage to the skin or hair.

Optionally, the pulsed light heat source forms a temperature gradient between the source and the skin.

Optionally, the pulsed heat source does not raise the volume of air to a temperature sufficient to damage hair or skin.

Optionally, the heat emitted from the pulsed heat source is insufficient in duration to raise the temperature of the skin or hair so that damage of hair or skin occurs.

Optionally, the apparatus includes a heat sensor that responds to the temperature of the skin and reduces the temperature of the skin and hair prior to the temperature rising to a level at which it causes damage to hair or skin.

In some embodiments of the present invention, the pulsed heat source is a pulsed heat and light source, for delivering pulsed radiation and heat by conduction to the skin.

Optionally, the pulsed heat and light source produces broad band pulsed light.

Optionally, the pulsed heat and light source includes a filter that filters the broad band pulsed light.

Optionally, the pulsed light and heat source is a flash lamp or an arc discharge lamp.

There is thus provided a method of treating acne comprising:

heating the skin and optionally the hair of a subject with pulsed heat;

conducting a portion of the heat to one or more acne-related structures from the skin and optionally from the hair; and at least partially destroying, by the conducted heat, of one or more acne related structures without causing damage to the skin.

Optionally, heating the skin and optionally the hair comprises heating on more than one occasion, separated by a period of time less than 10 minutes.

Alternatively, heating the skin and optionally the hair comprises optionally heating on more than one occasion, separated by a period of time less than 2 minutes.

Alternatively, heating the skin and optionally the hair comprises optionally heating on more than one occasion, separated by a period of time less than about 1 minute.

Alternatively, heating the hair and optionally the skin comprises optionally heating on more than one occasion, wherein each occasion is insufficient to cause full destruction of an acne-related structure.

Optionally, an acne-related structure comprises a structure associated with an acne focus.

Optionally, a portion of said heating is generated by coherent radiant energy.

Alternatively, at least a portion of said heating is optionally generated by incoherent radiant energy.

In some embodiments of the present invention, heating the skin and optionally the hair comprises:

heating the air outside the skin; and conducting heat by the skin and optionally the hair, to the one or more acne-related structures.

In some embodiments of the present invention, heating the skin and optionally the hair comprises heating the skin and the hair.

In some embodiments of the present invention, the acne comprises a focus without an associated hair external to the skin and wherein heating the hair and optionally the skin comprises heating the skin.

Optionally, heating the skin and optionally the hair comprises heating the skin and the hair.

Optionally, the acne comprises a focus without an associated hair external to the skin and wherein heating the hair and optionally the skin comprises heating the skin.

In some embodiments of the present invention, an acne related structure optionally comprises an acne cyst or nodule.

Alternatively, an acne related structure optionally comprises a sebaceous gland.

Alternatively, an acne related structure optionally comprises a papilla.

Alternatively, an acne related structure optionally comprises an acne papule.

Alternatively, an acne related structure optionally comprises an acne pistule

Alternatively, an acne related structure optionally comprises an intrafollicular hyperkeratosis.

Alternatively, an acne related structure optionally comprises a sweat gland.

Alternatively, an acne related structure optionally comprises a hemorhagic follicular plug.

Alternatively, an acne related structure optionally comprises a blockage.

Alternatively, an acne related structure optionally comprises a bacterium.

Alternatively, an acne related structure optionally comprises a *Propionibacterium acnes* bacterium.

Alternatively, an acne related structure optionally comprises a pilosebaceous follicular blockage.

Alternatively, an acne related structure optionally comprises a pilosebaceous follicular blockage comprising a closed comedone (whitehead).

Alternatively, an acne related structure optionally comprises a pilosebaceous follicular blockage comprising an open comedone (blackhead).

Alternatively, an acne related structure optionally comprises a pseudofolliculitis.

BRIEF DESCRIPTION OF THE DRAWINGS

Exemplary non-limiting embodiments of the invention are described in the following description, read with reference to the figures attached hereto. In the figures, identical and similar structures, elements or parts thereof that appear in more than one figure are generally labeled with the same or similar references in the figures in which they appear. Dimensions of components and features shown in the figures are chosen primarily for convenience and clarity of presentation and are not necessarily to scale. The attached figures are.

DESCRIPTION OF EXEMPLARY EMBODIMENTS

Figure 1:
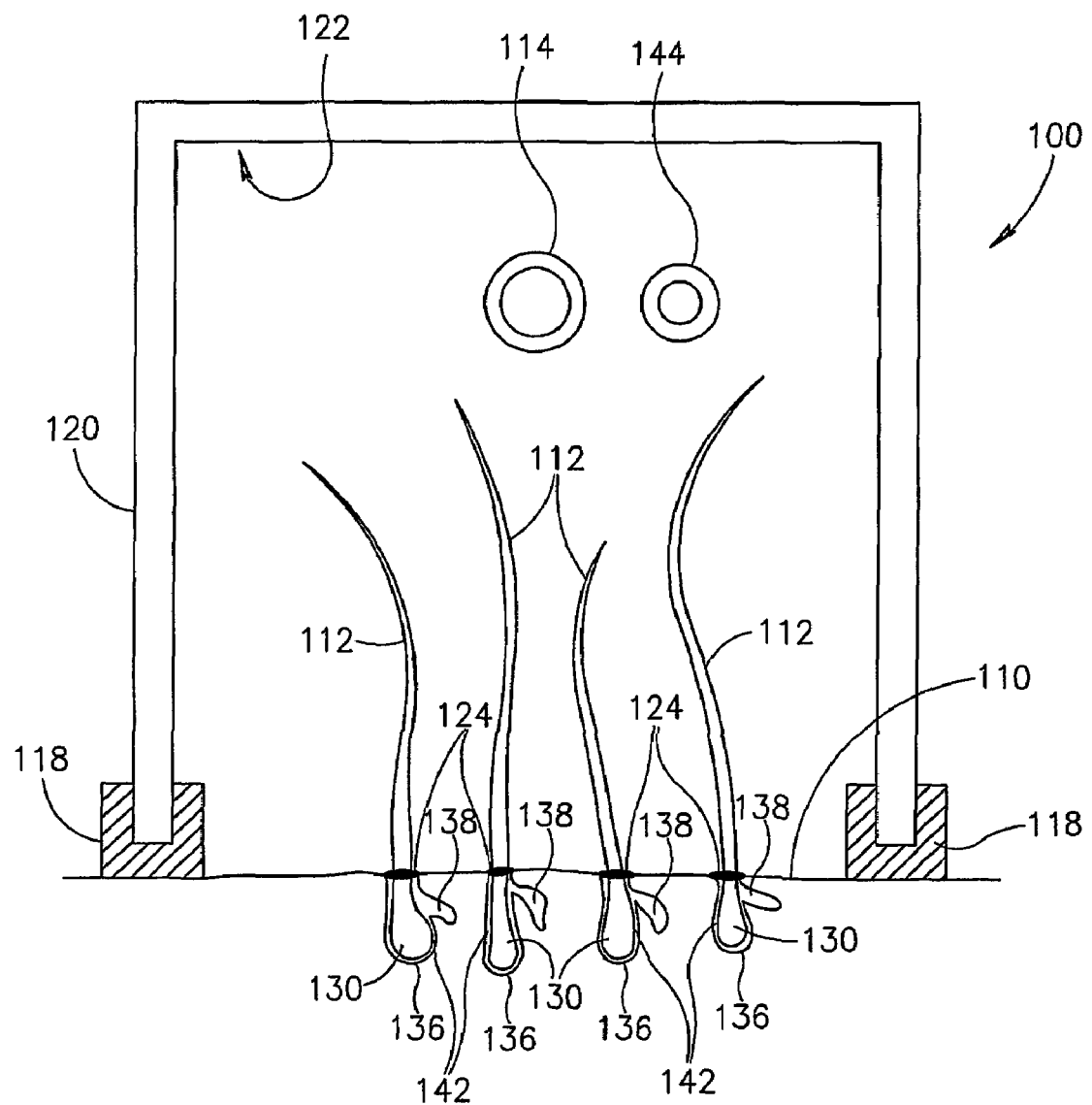
FIG. 1 is a schematic diagram of an embodiment of the device of the present invention treating an area of skin including hair and related structures on a first occasion.

FIG. 1 is a schematic diagram of an embodiment of an exemplary heating device 100 of the present invention for treating acne. Heating device 100 applies heat to an area of skin 110 and hairs 112, raising their temperature and causing the amelioration or resolution of acne symptoms.

In an exemplary embodiment, heating device 100 has a radiant heat source 114 that provides pulsed radiant heat energy that is absorbed by hairs 112 and skin 110. Optionally, heating device 100 has a housing 120 that has a mirrored surface 122 designed to increase the heat efficiency of pulsed radiant heat source 114. Additionally or alternatively, housing 120 has a gasket 118 that serves to seal housing 120 against the skin so relatively small amounts of heat escape. Optionally, heating device 100 also includes a second monochromatic radiant heat source 144 that is turned on when the skin reaches a pre-determined temperature, for example, 60° C., to selectively heat the hair.

In an exemplary embodiment, radiant energy source 144 is a laser beam of substantially monochromatic radiant energy. Such a prior art system for hair removal is disclosed by Zaias in U.S. Pat. No. 5,059,192.

Optionally, radiant heat source 114, is a pulsed dye laser such as the Sclero-LASER, manufactured by Candela Corp. of Wayland, Mass.

In an exemplary embodiment, such radiant energy source has a time application according to the prior art application of Eckhouse, EPO 736308, on the order of 10 to 100 msec and energy fluence on the order of 10 to 100 J/cm$^2$. In an alternative embodiment taught by this prior art, each step is repeated with at least two angular divergences being used, thus obtaining at least two depths of penetration.

In an alternative embodiment taught by this prior art for depilation, a gel or other suitable fluid material is applied to skin 110 to cool skin 110 so that the radiant energy is absorbed primarily by hair 112 and conducted into a follicle 142.

Alternatively or additionally, pulsed radiant heat source 114 provides heat according to the subject skin type. As shorter wavelengths do not readily pass into the skin, filters that cut off shorter wavelengths for various skin pigmentations are optionally utilized. For example, a cut off wavelength of 600 nm is used when the subject has fair skin while a cut off in the range of 700 to 800 nm is used for people with dark skin.

Figure 2:
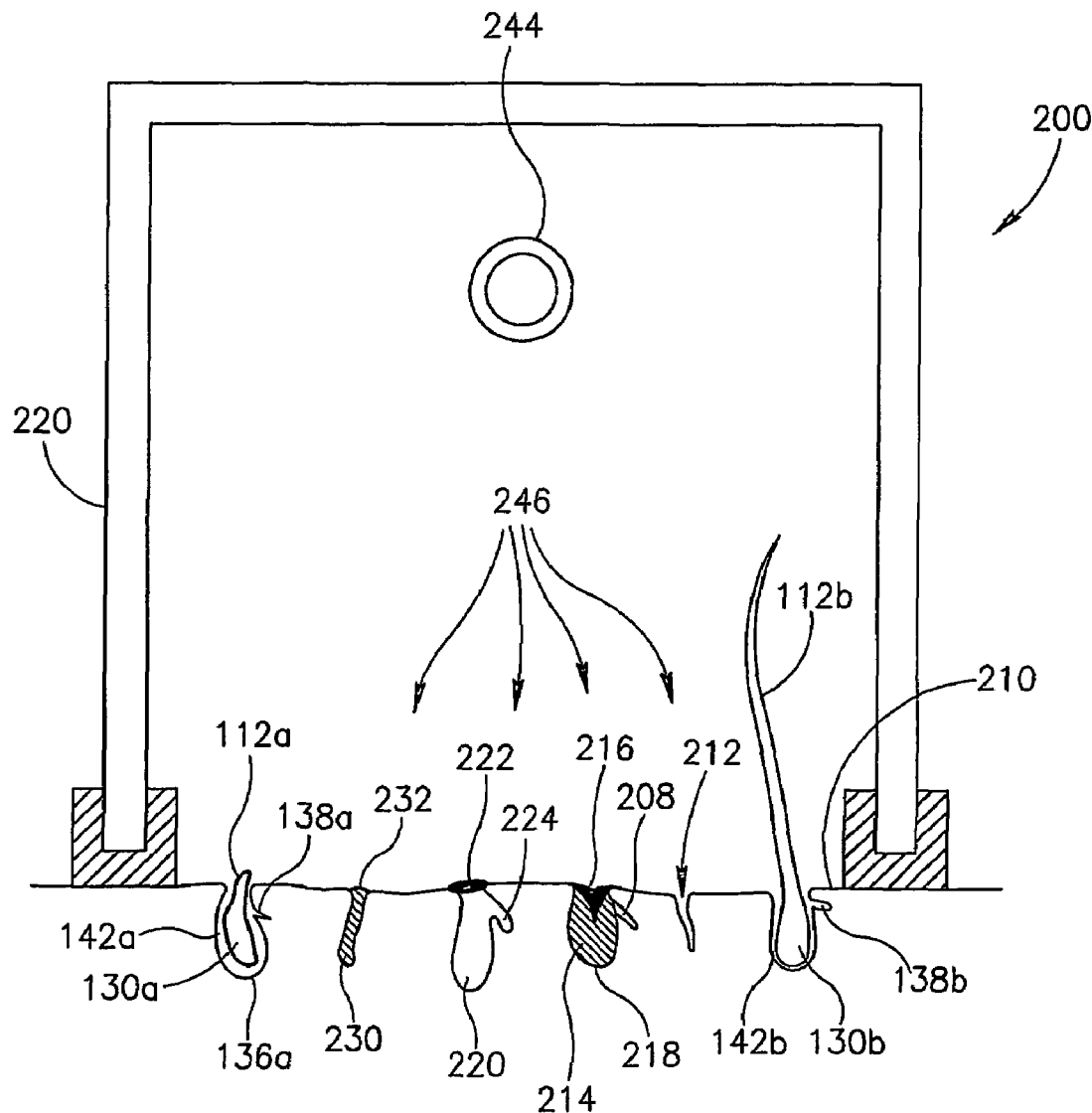
FIG. 2 is a schematic diagram of an embodiment of the device of the present invention treating an area of skin including hair and related structures on subsequent occasions.

In an alternative embodiment of the invention, as shown for example in FIG. 2, a heat source 244 provides non-radiant energy 246, for example pulsed heat, which heats the air surrounding the skin. Optionally, heat source 244 provides radiant energy 246, for example that is pulsed. In practice a single source, such as a pulsed flash lamp, can provide both sources of heat. In such a device, the pulsed radiant energy reaches the skin first and pre-heats the hair and skin. Heat from the lamp is conducted towards the skin and heats the hair and skin. However, heat is removed from the skin before the temperature is high enough to damage the skin, by blowing cooler air across the skin, drawing the hot air from the enclosure or by removing the enclosure from the skin. This type of device is taught, for example, by U.S. Pat. No. 6,187,001.

In an exemplary embodiment, radiant energy source 114 is a xenon arc lamp with a glass tube or any other flash lamp as taught, for example, in prior art U.S. Pat. No. 6,187,001. When flashed, the lamp emits broadband electromagnetic radiation that is absorbed by the skin and hair to provide pre-heating.

Additionally or alternatively, the source is a quartz flash lamp in conjunction with a filter. Such filter removes light between 100-400 nm that cause damage to the skin.

Alternatively or additionally heating source 100 is provided with enhancements to its energy delivery. For instance, surface 122 is a parabolic reflector that aids in the spreading of the radiant energy from source 114 and/or source 144 or source 244. Alternatively or additionally, a concave lens is provided to collimate the broadband/or radiant energy so that substantially all the energy emitted by lamp is directed at the target and surrounding tissue.

The object of any chosen source is that though there is destruction of a hair and sebaceous gland and acne-related structures, the heat does not cause damage to skin 110. This is because the radiant energy is not turned on long enough to damage the surrounding tissue, but merely conducts for a brief period through hair 112 and/or acne related structures. Alternatively or additionally, the skin is not damaged because skin 110 and hair 112 are preheated, the gradient between the treated structures and the surrounding skin 110 is small; therefore, the rate of heat flow to the surrounding tissue is minimal.

Alternatively or additionally the present invention contemplates using any heat source that destroys the hair by heating it selectively.

In an exemplary embodiment, the present invention uses depilation to cause acne symptoms ameliorate or cease. To destroy or partially destroy hair, pulsed radiant heat is conducted by hair 112 to bulb 130 so hair 112 falls out. Additionally, the heat is conducted by hair 112 to destroy or partially destroy pilosebaceous plug 124, sebaceous gland 138 and acne-related structures and the P. acnes that resides in these structures.

Additionally, the heat destroys or partially destroys hair 112 and causes the sebum 142 and keratin within the acne-related structures to flow, allowing drainage of these structures. P. acnes is an anaerobic bacterium that is destroyed by exposure to oxygen. The flow of material out of the space around bulb 136, not only partially clears the source of food for P. acnes, but allows oxygen to enter bulb space 136, and sebaceous gland 138 and related structures, killing the P. acnes bacteria FIG. 2 is a schematic diagram of an embodiment of a heating device 200 of the present invention treating an area of skin 110 including hair and related structures on subsequent occasions.

As described above, the hair is destroyed, by any method, in a first treatment. Thereafter, heat source 244, on a second or further subsequent treatment (which may be spaced from the first treatment by days or weeks), causes partial destruction of one or more acne-related structures on an area of skin 210, to ameliorate the acne infection, this can be, used, at a lower power than used in the initial treatment above.

For example, a follicle 212, with the hair destroyed by heat source 244, is opened by the second application of energy, allowing drainage of any sebum, keratin or fluids. A follicle 214 containing sebum 218 with the hair destroyed shows a hemorhagic plug 216 that has formed as a result of depilation and is now being treated by a subsequent treatment from heating source 244. Sebum 218, because it is not exposed to air, has become a base for a P. acnes infection and is in the process of reforming an acne pustule.

A follicle 220, with the hair destroyed, has a small pilosebaceous plug 222 that has formed following a first treatment, and is just beginning to plug follicle 220 so that the sebum produced by a sebaceous gland 224 becomes trapped, followed by infection by P. acnes infection. Heating source 224 is now being used to open plugged follicle 220. A follicle 230, with the hair destroyed, has filled fully with some hemorhagic debris 232 that holds in fluid and leads to infection formation. Again, heating source 224 is being used to remove the hemorhagic debris 232 so that the acne infection will continue to resolve.

In an exemplary embodiment, in this second treatment, heat source 244 sends heat 246 to blockages within follicles, 214, 220 and 230 so that they break up and P. acnes bacteria is removed either through loss of metabolic food source or through the action of oxygen.

Partial destruction of acne-related structures results in incomplete reformation of the pilosebaceous plug and reduced bacterial growth, minimizing the severity of acne inflammation. Subsequent treatments open follicles, causing acne symptoms to further ameliorate or cease.

FIG. 2 also contains a schematic diagram of an embodiment of the device of the present invention treating an area of skin including hair and related structures on repeated occasions according to an alternative embodiment of the device of the present invention. According to this embodiment of the invention, the hair is not destroyed.

When an exemplary device of FIG. 2 is used for treating acne, with the destruction of hair, the radiant energy level supplied by the flash lamp is generally in a range of 6-7.5 J/cm$^2$ (a total light energy of about 75 J), the level of electrical energy supplied to the flash lamp is 520-600 J, and the heat energy is 450-530 J. These values are representative and other, mainly higher values, may be used. The inventors have found that a single such treatment is usually effective to both destroy the hair and to destroy the acne, such that subsequent treatments are not usually necessary.

In order not to destroy the hair, lower levels of energy are used. Such lower levels are also possible in subsequent treatments after destruction of the hair, as described above.

For example, for the same device used to destroy the hair, an electrical input of 350-420 J, provides a radiant energy level of 3.4 J/cm$^2$, and light energy of about 50 J and a heat energy of about 300-370 J. However, the energy levels useful in this embodiment of the invention are broader than these values and any energy level that is below a destruction threshold of the hair can be used, so long as it is high enough to heat the acne related structures to a level high enough to destroy them. For instance a radiant energy level of 2 J/cm$^2$ can be used.

Such an energy source is passed over the skin on two or more occasions, such as five times, within a short span of time, such as with a minute delay between each application. These two or more applications can be repeated on several occasions such as, for instance, six occasions of multiple applications over a period of three weeks. The multiple treatments of hairs such as hair 112a and hair 112b, result in partial destruction or drainage of acne-related structures, to ameliorate the acne infection.

It is believed that the relatively closely spaced treatments each heat the pilosebaceous plug or other lipid rich structures to a given temperature, that is not high enough to destroy the structures. However, due to the high heat capacity of the lipid tissue, the second treatment further heats the lipid tissue to a higher temperature. However, the ordinary tissue is cooled during the interval so that the temperature of this tissue does not rise above the temperate in the first treatment. However, other more complex mechanisms may be responsible for the results.

Without a pilosebaceous plug, the sebum 142a and P. acnes drain from a follicular area 136a around hair bulb 130a and from a follicular area 142b around hair bulb 130b to ameliorate the acne infection. Additionally or alternatively, with destruction and/or partial destruction of sebaceous gland 138a and 138b, the sebum 142a does not build up further, allowing amelioration of the acne infection. Additionally or alternatively, other acne-related structures are destroyed, partially destroyed and/or drained to ameliorate the acne condition. Acne-related structures include but are not limited to one or more of the following: a papilla, an acne cyst or nodule, an acne papule, an acne pistule, intrafollicular hyperkeratosis, a pseudofolficulitis (ingrown hair), a sweat gland, a sweat gland duct or a hemorhagic follicular plug.

Sebaceous gland 138 and pilosebaceous plug 124 and P. acnes are structures that are destroyed at a lower temperature than hair 112. Therefore, sebaceous gland 138, pilosebaceous plug 124 and P. acnes are destroyed or partially destroyed due to conduction of heat from skin 110 and/or hair 112 even when the heat is insufficient to destroy hair 112. Further, these structures appear to retain heat longer than the skin and hair, so the multiple applications of heat spaced a minute apart, causes a heat buildup in these structures sufficient to cause damage to them, but insufficient to cause damage to the skin and hair.

Alternatively or additionally, melanocytes contained within follicles 230, 220 and 214 absorb the radiant energy, and the energy is conducted from the melanocytes within follicles 230, 220 and 214 to kill the P. acnes bacteria without damaging the skin or hair.

While the invention has been described with respect to limited number of embodiments, it will be appreciated that many variations, modifications and other applications of the invention may be made. Also, combination of elements from variations may be combined and single elements may be used. Any and all such variations and modifications, as well as others that may become apparent to those skilled in the art are intended to be included within the scope of the invention, as defined by the appended claims.

The terms "include", "comprise" and "have" and their conjugates as used herein mean "including but not necessarily limited to."

It will be appreciated by a person skilled in the art that the present invention is not limited by what has thus far been described. Rather, the scope of the present invention is limited only by the following claims.

The invention claimed is:

1. A method of treating acne comprising:
    destroying a hair associated with a focus of acne using heat on a first occasion; and
    pulsed heating the focus of acne on a second occasion to at least partially destroy an acne-related structure,
    wherein heating on a second occasion comprises:
    heating a hair associated with a focus of acne; and
    conducting energy from the hair to at least one acne-related structure to at least partially destroy the structure without causing damage to the skin or hair.

2. A method according to claim 1, wherein an acne-related structure comprises a structure associated with the acne focus.

3. A method according to claim 1, wherein at least a portion of said heating on a second occasion is generated by coherent radiant energy.

4. A method according to claim 1, wherein at least a portion of said heating on a second occasion is generated by incoherent radiant energy.

5. A method according to claim 1, wherein heating a hair comprises:
    heating the air outside the skin; and
    conducting heat by the hair to the acne-related structure, to at least partially destroy the structure without causing damage to the skin or hair.

6. A method according to claim 1, wherein at least a portion of said heating is generated by coherent radiant energy incident on the skin.

7. A method according to claim 1, wherein at least a portion of said heating is generated by incoherent radiant energy incident on the skin.

8. A method according to claim 1, wherein at least a portion of said heating is generated by conduction of heat from air outside the skin.

9. A method according to claim 1, wherein at least a portion of said heating is generated by radiant energy that preferentially heats the focus or sebum associated with the focus as compared to the skin.

10. A method according to claim 1 wherein an acne related structure comprises an acne cyst or nodule.

11. A method according to claim 1 wherein an acne related structure comprises a sebaceous gland.

12. A method according to claim 1 wherein an acne related structure comprises a papilla.

13. A method according to claim 1 or wherein an acne related structure comprises an acne papule.

14. A method according to claim 1 or wherein an acne related structure comprises an acne pistule.

15. A method according to claim 1 or wherein an acne related structure comprises an intrafollicular hyperkeratosis.

16. A method according to claim 1 or wherein an acne related structure comprises a sweat gland.

17. A method according to claim 1 or wherein an acne related structure comprises a hemorhagic follicular plug.

18. A method according to claim 1 or wherein an acne related structure comprises a blockage.

19. A method according to claim 1 or wherein an acne related structure comprises a bacterium.

20. A method according to claim 1 or wherein an acne related structure comprises a *Propionibacterium acnes* bacterium.

21. A method according to claim 1 or wherein an acne related structure comprises a pilosebaceous follicular blockage.

22. A method according to claim 1 or wherein an acne related structure comprises a pilosebaceous follicular blockage comprising a closed comedone (whitehead).

23. A method according to claim 1 or wherein an acne related structure comprises a pilosebaceous follicular blockage comprising an open comedone (blackhead).

24. A method according to claim 1 or wherein an acne related structure comprises a pseudofolliculitis.

* * * * *